(12) United States Patent
Thompson

(10) Patent No.: US 7,429,255 B2
(45) Date of Patent: *Sep. 30, 2008

(54) CLOSED LOOP MEDICAMENT PUMP

(75) Inventor: David L. Thompson, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 844 days.

This patent is subject to a terminal disclaimer.

(21) Appl. No.: 10/747,832

(22) Filed: Dec. 29, 2003

(65) Prior Publication Data

US 2004/0147872 A1     Jul. 29, 2004

(51) Int. Cl.
*A61M 31/00*     (2006.01)
(52) U.S. Cl. ........................................ 604/67
(58) Field of Classification Search ................ 604/30, 604/31, 65, 66, 67, 70, 93.01, 890.1, 891.1; 128/DIG. 12, DIG. 13
See application file for complete search history.

(56) References Cited

U.S. PATENT DOCUMENTS

| | | | |
|---|---|---|---|
| 3,943,918 A | 3/1976 | Lewis | |
| 4,406,658 A | 9/1983 | Lattin et al. | |
| 4,692,147 A | 9/1987 | Duggan | |
| 4,714,462 A | 12/1987 | DiDomenico | |
| 4,838,887 A | 6/1989 | Idriss | |
| 4,987,897 A | 1/1991 | Funke | |
| 5,113,859 A | 5/1992 | Funke | |
| 5,140,985 A | 8/1992 | Schroeder et al. | |
| 5,279,543 A | 1/1994 | Glikfeld | |
| 5,326,652 A | 7/1994 | Lake | |
| 5,362,307 A | 11/1994 | Guy et al. | |
| 5,489,624 A | 2/1996 | Kentner et al. | |
| 5,536,768 A | 7/1996 | Kentner et al. | |
| 5,558,957 A | 9/1996 | Datta et al. | |
| 5,569,186 A | 10/1996 | Lord et al. | |
| 5,591,217 A | 1/1997 | Barreras | |
| 5,661,393 A | 8/1997 | Sengupta | |

(Continued)

FOREIGN PATENT DOCUMENTS

WO      WO 91/07680     5/1991
WO      WO 96/00110     1/1996

OTHER PUBLICATIONS

European Search Report for EP 1 048264 A1.

*Primary Examiner*—Manuel A Mendez
(74) *Attorney, Agent, or Firm*—Banner & Witcoff, Ltd.

(57) ABSTRACT

A device to determine the level of a substance of interest in a patient's body and provide a therapeutic amount of medicament is disclosed. The level of a substance of interest in the patient's body is determined by iontopheretically sampling the patient's blood and then analyzing the resulting sample to determine the level of the substance of interest. The information about the level of a substance of interest is transmitted to an implanted drug pump in the patient's body. In the preferred embodiment, the substance of interest sensor is an external sensor applied to the user's skin.;: In an alternate embodiment, the sensor may be implanted. The preferred method of transmitting information about the level of a substance of interest determined by the sensor is transmitted to an implanted drug pump in the patient's body is via a so called "body bus". The "body bus" is a telemetry system where the patient's own body provides the interconnection between the iontopheretic device and the implanted drug pump.

30 Claims, 7 Drawing Sheets

U.S. PATENT DOCUMENTS

| | | |
|---|---|---|
| 5,683,432 A | 11/1997 | Goedeke et al. |
| 5,713,923 A | 2/1998 | Ward et al. |
| 5,730,714 A | 3/1998 | Guy et al. |
| 5,733,313 A | 3/1998 | Barreras, Sr. et al. |
| 5,862,803 A | 1/1999 | Besson et al. |
| 5,978,702 A | 11/1999 | Ward et al. |
| 6,128,537 A | 10/2000 | Rise |
| 6,669,663 B1 * | 12/2003 | Thompson .................. 604/67 |

* cited by examiner

CLOSED LOOP MEDICAMENT PUMP

This application claims priority to U.S. application Ser. No. 09/302,593, filed Apr. 30, 1999, issued on Dec.30, 2003 as U.S. Pat. No. 6,669,663, which is incorporated herein by reference in its entirety.

BACKGROUND OF THE INVENTION

1. Field of the Invention

The invention relates to a device for treating physiological conditions and more particularly relates to a device for treating diabetes or other physiological conditions through the use of a closed loop control device for sensing diabetic or other physiologic states and for delivering an appropriate amount of insulin or other appropriate medicament or drug, if required, from an implanted drug pump.

2. Description of Related Art

Diabetes is a disease where the body does not produce or properly use insulin, a hormone that is needed to convert carbohydrates such as sugar or starches into energy needed for daily life. It is not clear what causes diabetes, but both genetics and environmental factors such as obesity and lack of exercise seem to play roles.

There are two major types of diabetes: Insulin-Dependent (type I) and Non-Insulin-Dependent (type II). It is estimated that diabetes, in its various forms, affects 16 million people in the United States alone. In the United States, approximately 1,700 people are diagnosed with diabetes every day with about 625,000 people diagnosed in a year. Type II diabetes is the most common form of the disease accounting for about 90-95 percent of all diabetes cases. Type I diabetes accounts for 5-10 percent of all cases of diabetes.

Insulin-Dependent (type I) diabetes is an autoimmune disease where the body does not produce any insulin. This disease occurs most often in the first two decades of life but can develop up to about age 40. People with this type of diabetes must take daily insulin injections to stay alive.

Non-Insulin-Dependent (type II) diabetes is a metabolic disorder resulting from the body's inability to make enough of or properly use insulin. Environmental factors such as obesity and lack of exercise appear to play a large role in this type of diabetes. Because many American adults are overweight and don't exercise, type II diabetes is nearing epidemic proportions in the US. Non-Insulin Dependent diabetes usually gradually develops after about age 35.

Diabetes is the fourth-leading cause of death by disease in the United States. The American Diabetes Association estimates that more than 169,000 died from the disease and its related complications in 1997. Some of the complications associated with diabetes are blindness, kidney disease, nerve disease, amputations, heart disease and stroke.

Diabetes is the leading cause of new cases of blindness in people ages 20-74. Each year, it is estimated that from 12,000 to 24,000 people lose their sight because of diabetes. Ten to twenty-one percent of all people with diabetes develop kidney disease. In 1992, an estimated 19,800 people initiated treatment for end stage renal disease (kidney failure) because of diabetes.

In addition, about 60-70 percent of people with diabetes have mild to severe forms of diabetic nerve damage. In severe forms, this nerve damage can lead to lower limb amputations. Diabetes is the most frequent cause of non-traumatic lower limb amputations. The risk of a leg amputation due to nerve damage is 15-40 times greater for a person with diabetes than for a person without diabetes. Each year, an estimated 54,000 people lose their foot or leg to diabetes related amputations.

People with diabetes are two to four times more likely to have heart disease than those who don't have diabetes. Heart disease is present in 75 percent of diabetes-related deaths. Annually, diabetes related heart disease is estimated to cause more than 77,000 deaths. Further, people with diabetes are two to four times more likely to suffer a stroke than people without diabetes.

The American Diabetes Association estimates diabetes to be one of the most costly health problems in America. Health care and related costs for treatment, as well as the opportunity costs of lost productivity are estimated to be nearly $92 billion annually.

U.S. Pat. No. 5,569,186, issued to Peter C. Lord and Fredric C. Coleman on Oct. 29, 1996, entitled "Closed Loop Infusion Pump System with Removable Glucose Sensor" discloses an infusion pump system having a removable in vivo glucose sensor and an implantable infusion pump. The glucose sensor determines the concentration of glucose in the user's blood and then signals the implanted pump to deliver a selected amount of medication, such as insulin, to the user. Signaling is accomplished via a direct or telemetric connection between the sensor and the pump.

U.S. Pat. No. 5,279,543, issued to Glikfeld et al. on Jan. 18, 1994, discloses an iontophoretic device to determine the level of glucose in a user's body combined with an insulin pump or iontophoretic delivery system and feedback to administer appropriate levels of a insulin to diabetic patients.

It has been a goal of those developing medical devices to treat diabetes to produce a fully implantable system that mimics the body's own system for regulating glucose. Such a system would require a sensor to sense the level of glucose in the blood, a device to infuse insulin or similar hormone to control the level of glucose and means for relaying the results of the glucose sensed to the device to infuse insulin so that a closed loop is formed. In this way, the system would automatically react to different levels of glucose and provide an appropriate level of insulin.

Unfortunately, such a fully implantable system has not yet been created. Much work has been done to develop ChemFETs and other sensors that can detect the level of glucose in the blood. However, when implanted, these sensors only have a lifespan of a few days at best. To be practical, implantable sensors to detect the level of glucose in the blood need to have a lifespan of at least several months.

SUMMARY OF THE INVENTION

A device to determine the level of glucose in a patient's body and provide a therapeutic amount of insulin or a similar drug is disclosed. The level of glucose in the patient's body is determined by painlessly iontophoretically sampling the patient's blood and then analyzing the resulting sample to determine the level of glucose. The information about the level of glucose is transmitted to an implanted drug pump in the patient's body. In the preferred embodiment, the glucose sensor is an external sensor applied to the user's skin. In an alternate embodiment, the sensor may be implanted. The preferred method of transmitting information about the level of glucose determined by the sensor is transmitted to an implanted drug pump in the patient's body is via a so called "body bus". The "body bus" is a telemetry system where the patient's own body provides the interconnection between the iontophoretic device and the implanted drug pump.

It is therefore a primary object of the invention to provide a system that mimics the body's own system for administering an appropriate dose of insulin.

It is another object of one embodiment of the invention to provide a system that mimics the body's own system for administering an appropriate dose of insulin including an external sensor.

These and other objects of the invention will be clear from the description of the invention given herein and particularly with reference to the attached drawings and the Detailed Description of the Invention. Throughout this description, like reference numbers refer to like elements.

DETAILED DESCRIPTION OF THE INVENTION

Figure 1:
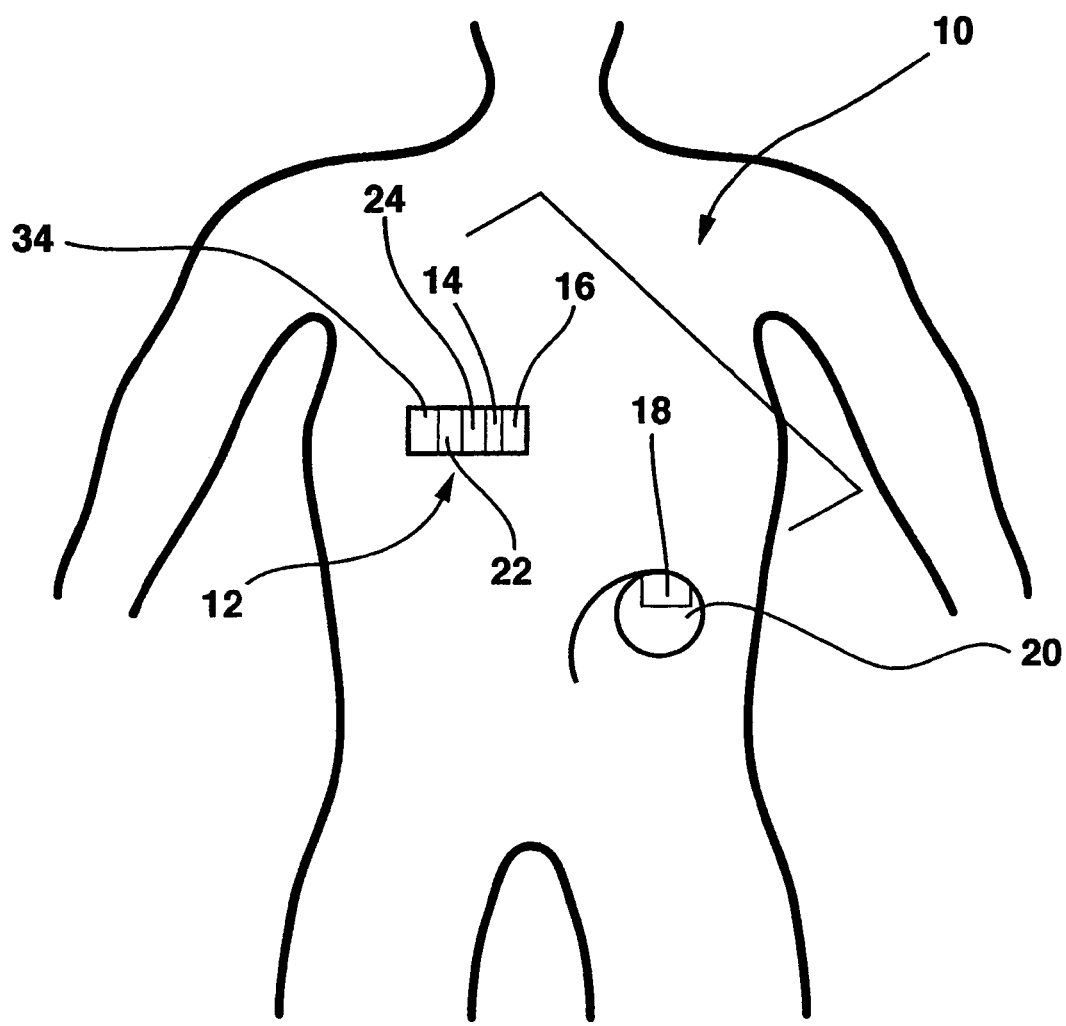
FIG. 1 is a perspective schematic view of the present invention in use on a patient's body.
Figure 2:
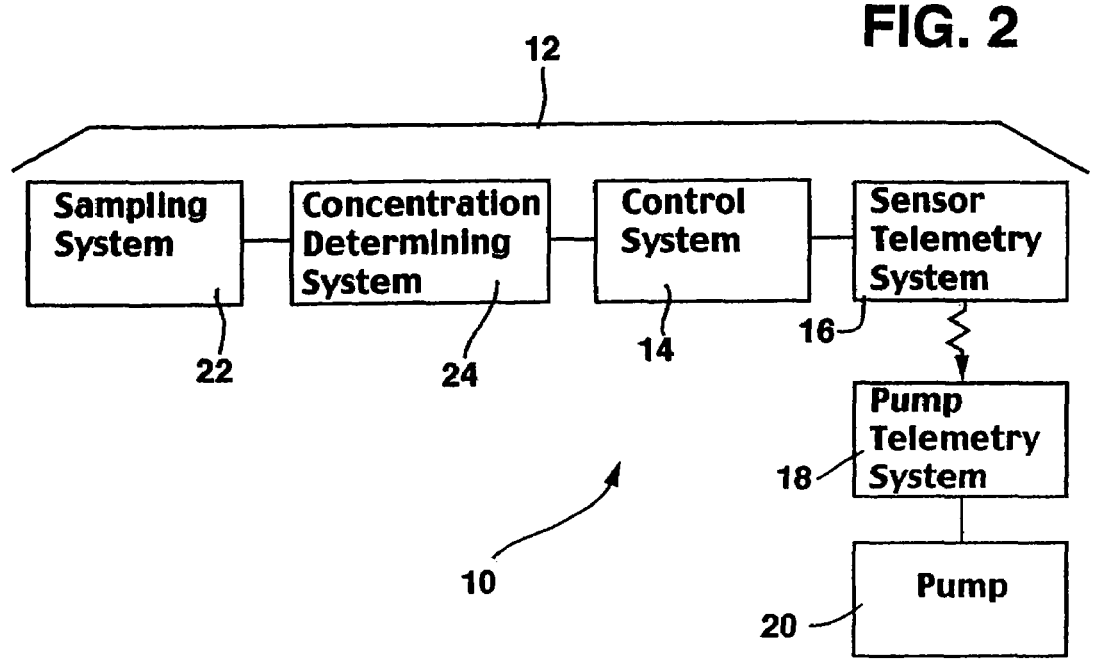
FIG. 2 is a block diagram of the preferred embodiment of the present invention.

Referring to FIG. 1, the invention is shown generally labeled 10. The invention 10 includes a sensor module 12, a control system 14, a sensor telemetry system 16, a pump telemetry system 18 and an implantable drug pump 20.

In the preferred embodiment, the purpose of sensor module 12 is to non-invasively sample glucose from blood, determine the concentration of glucose in the blood, determine the appropriate dose of insulin to be administered to the user and communicate the determined dose to an implantable drug pump 20. Consequently, the glucose sampling and glucose concentration determining function of sensor module 12 is performed by two parts, a sampling system 22 and a concentration determining system 24. The non-invasive glucose sampling is preferably performed by sampling system 22 by iontopheretically removing glucose from blood through the skin. The preferred device for sampling system 22 is shown in U.S. Pat. No. 5,730,714 issued on Mar. 28, 1998 to Richard Guy, Girish Rao, Peretz Glikfeld, Christopher Cullander and Robert S. Hinz entitled "Method for the Iontopheretic Non-Invasive Determination of the In Vivo Concentration of Glucose", the teaching of which is incorporated herein in its entirety. Other examples of iontopheretic sampling parts 22 to remove glucose molecules through the skin that could be used in the present invention are disclosed in U.S. Pat. No. 4,406,658 issued on Sep. 27, 1983 to Gary A. Lattin and Richard Spevak entitled "Iontopheretic Device with Reversible Polarity", U.S. Pat. No. 5,279,543 issued on Jan. 18, 1994 to Peretz Glikfield, Christopher Cullander, Robert S. Hinz and Richard H. Guy entitled "Device for Iontopheretic Non-Invasive Sampling or Delivery of Substances" and U.S. Pat. No. 5,362,307 issued on Nov. 8, 1994 to Richard Guy and Girish Rao entitled "Method for the Iontopheretic Non-Invasive Determination of the In Vivo Concentration Level of an Inorganic or Organic Substance", the collective teachings of which are incorporated herein by reference in their entirety.

The preferred device for the concentration determining system 24 is also shown in the herein above referenced '714 patent to Guy et al. Another device for the concentration determining system 24 is disclosed in an article by Joseph Black, Michael Wiliness, Platen Atanasov and Ebtisam Wiliness entitled "Integrated sensor-telemetry system for in vivo glucose monitoring" (Sensors and Actuators B 31 (1996) 147-153), the teaching of which is incorporated herein by reference in its entirety.

Sensor module 12 is preferably an external sensor that is placed on the skin of the patient. In the preferred embodiment, sensor module 12 is intended to be disposable. In this way, an "old" sensor module 12 can be conveniently and easily removed and replaced with a "new" sensor module 12, for example, daily. In another embodiment, the sensor module 12 may be reusable. In this embodiment, sensor module 12 would be capable of being cleaned in ways well known to those in the art such as by autoclaving.

Figure 4:
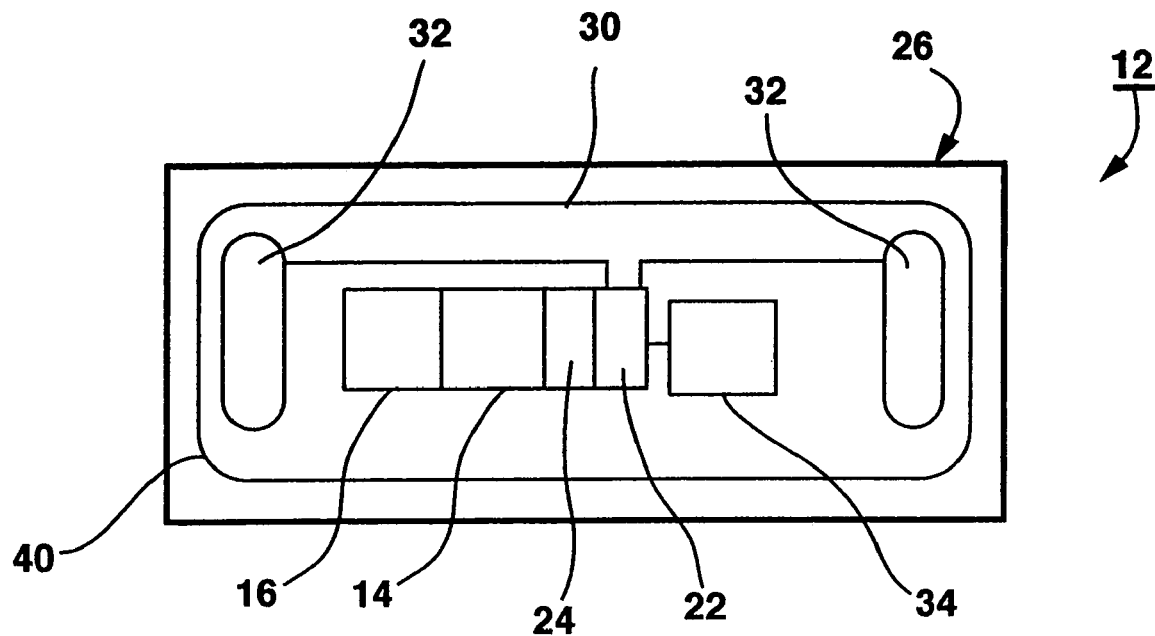
FIG. 4 is a plan view of a sensor of the present invention.
Figure 5:
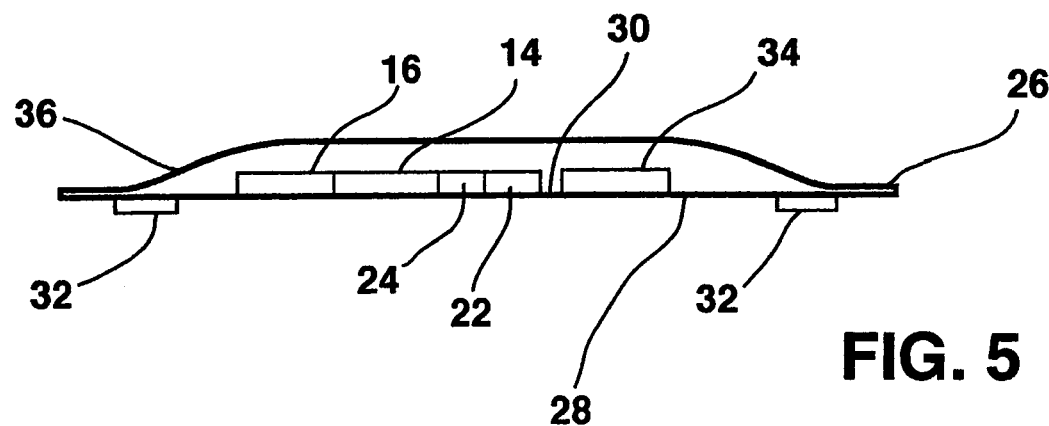
FIG. 5 is a side view of the sensor of FIG. 4.

Sensor module 12 is attached to a flexible substrate 26 (FIG. 4). Flexible substrate 26 has a patient contact side 28 and an instrumentation side 30. In particular, a pair of electrodes 32 that are part of the sampling system 22 are attached to the contact side 28 of flexible substrate 26 to come into contact with a user's skin. The contact side 28 has an adhesive that allows flexible substrate 26 to be removably attached to the skin of the user. The adhesive should be strong enough to cause the sensor module 12 to adhere to the skin of the patient but not so strong as to make it difficult to remove the sensor module 12 when desired as will be explained hereafter. The adhesive should also not be susceptible to iontopheresis. An example of such an adhesive is as substantially described in U.S. Pat. Nos. 5,489,624 and 5,536,768, both titled "Hydrophyllic Pressure Sensitive Adhesives" issued Feb. 6, 1996 and Jul. 16, 1996, respectively to Steven S. Kentner, Nancy J. Rustad and James S. Stabely, the collective teachings of which are incorporated herein by reference in their entireties.

Flexible substrate 26 may have a size and shape similar to that of commercially available disposable bandages. In one embodiment, flexible substrate 26 has a width dimension ranging between approximately 0.5" and approximately 3", and a length dimension ranging between approximately ¾" and approximately 5". Although the preferred embodiment of flexible substrate 26 is substantially rectangular, virtually any other shape for flexible substrate 26 is within the scope of the invention. For example, additional possible shapes for flexible substrate 26 include, but are not limited to, square, round and oval.

Instrumentation side 30 is on the opposite side of flexible substrate 26 than patient contact side 28. Instrumentation side 30 provides a surface for mounting the components of sensor module 12. In the embodiment illustrated in FIG. 4, flexible substrate 26 may comprise a resilient material upon which several electronic and electrical components are mounted. Flexible substrate 26 may include an integral or separate interconnect pattern of electrical conductors that provide for interconnection between the various components disposed on flexible substrate 26. Suitable materials that may be used to fabricate flexible substrate 26 include mylar, flexible foil, flex PC, Kapton and polymer thick film (PTF).

The components mounted to instrumentation side 30 include, in the preferred embodiment, the sampling system 22 and concentration determining system 24 of sensor 12, a battery 34, the control system 14 and the sensor telemetry system 16. Shown surrounding the components mounted to the instrument side 30 is an antenna 40 which receives downlinked telemetry programming data transmitted by an external programmer (not shown). Battery 34 is preferably mounted to flexible substrate 26 and powers sensor module 12, control system 14 and sensor telemetry system 16. Battery 34 is preferably a flexible battery such as a lithium manganese oxide (e.g., $LiMnO_2$) chemistry and may be of a sealed foil or plastic battery. In this way, battery 34 can bend with flexible substrate 26 as sensor module 12 is applied to the skin. Examples of such flexible batteries are disclosed in U.S. Pat. No. 5,558,957 issued to Madhav Datta and Ravindra V. Shenoy on Sep. 24, 1996 entitled "Method for Making a Thin Flexible Primary Battery for Microelectronics Applications" and U.S. Pat. No. 5,326,652 issued to Rickie C. Lake on Jul. 5, 1994 entitled "Battery Package and Method Using Flexible Polymer Films Having a Deposited Layer of an Inorganic Material", the collective teachings of which are incorporated herein by reference.

Control system 14 is preferably a microprocessor such as a low cost PIC microcontroller from Microchip Technology of Chandler, Ariz. Control system 14 is connected to concentration determining system 24 to receive information about the concentration of glucose determined by the concentration determining system 24. Control system 14 processes information from the concentration determining system 24 and determines an appropriate response according to the process shown in the flow chart of FIG. 6 as will be explained below.

A protective cover 36 attaches to and covers the components of sensor module 12. The function of protective cover 36 is to cover and protect the components on flexible substrate 26. As such, protective cover is preferable also flexible to allow strip 26 to be conformably attached to the patient's skin.

As mentioned, the invention includes an implantable pump 20. Pump 20 stores and delivers insulin or other appropriate drug to the patient through a catheter 38 in response to the information provided from sensor module 12. Pump 20 is preferably a peristaltic pump such as that disclosed in U.S. Pat. No. 4,692,147, issued on Sep. 8, 1987 to Stephen R. Duggan entitled "Drug Administration Device", the teachings of which are incorporated herein in its entirety. Such a pump is the Synchromed® Drug Pump, manufactured by Medtronic, Inc. of Minneapolis, Minn. modified as described in the '897 patent to receive information from sensor module 12. Catheter 38 may be the models 8700A, 8700B, 8702 or 8770 manufactured by Medtronic, Inc. of Minneapolis, Minn.

Although a peristaltic drug pump is preferred, any type of implantable pump may be used and is within the scope of the invention. Examples of alternate types of pumps 200 are disclosed in U.S. Pat. No. 4,714,462, issued on Dec. 22, 1987 to Robert A. DiDomenico and entitled "Positive Pressure Programmable Infusion Pump" and U.S. Pat. No. 4,838,887, issued on Jun. 13, 1989 to Samir F. Idriss and entitled "Programmable Valve Pump", the teachings of which are incorporated herein in their entirety.

Figure 6:
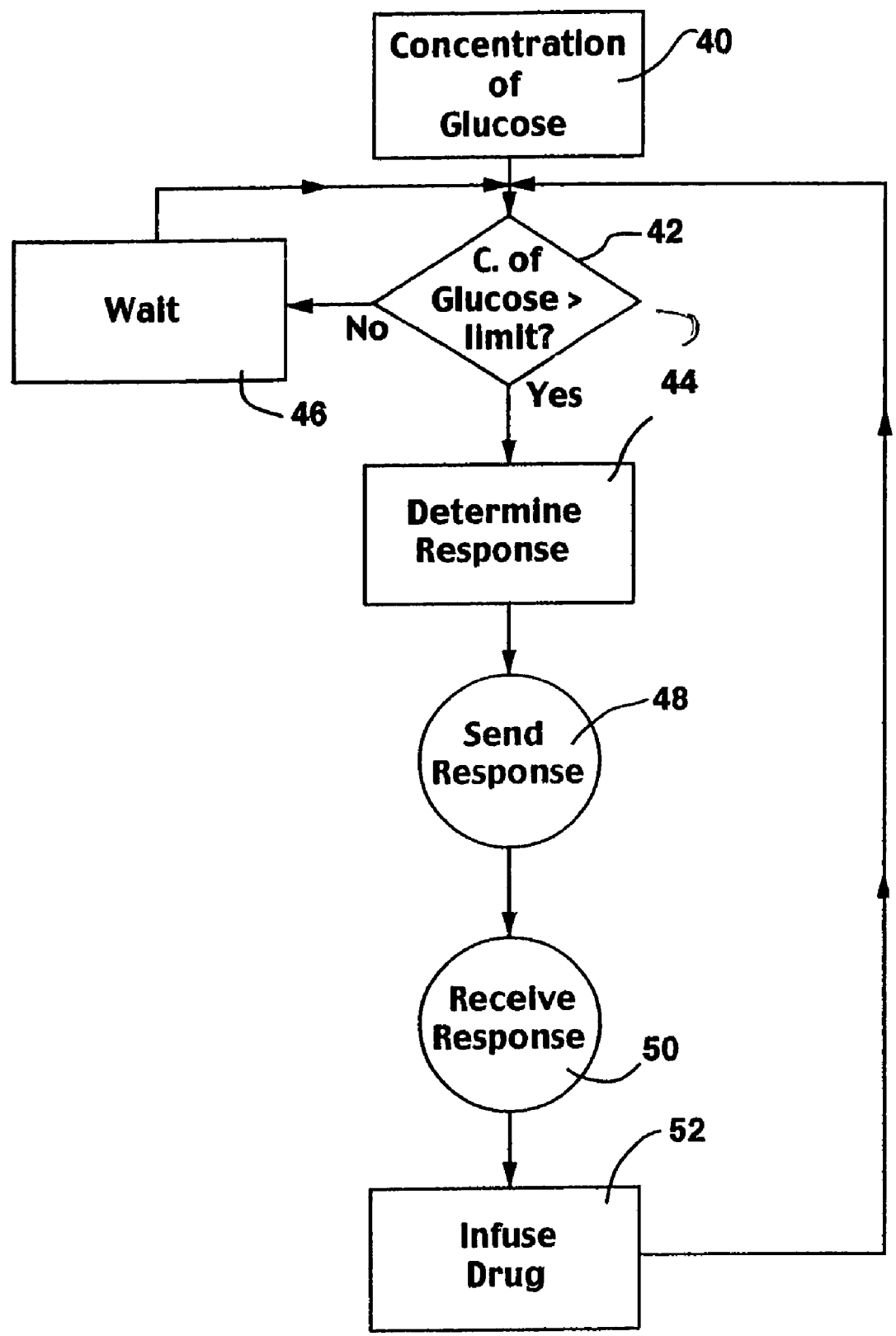
FIG. 6 is a flow chart of the preferred operation of the control system of the present invention that corresponds the embodiment shown in FIG. 2.

In FIG. 6, information about the determined concentration of glucose by sensor 12 is presented to step 40. The program passes from step 40 to step 42. Step 42 periodically compares the concentration of glucose presented at step 40 to a predetermined limit. The predetermined limit may be preset or set by downloading a desired limit. If the determined concentration in step 40 exceeds the predetermined limit, the program passes to step 44. If the determined concentration in step 40 does not exceed the preset limit, no action is taken and step 42 proceeds to step 46 to wait for an appropriate period to expire before passing to step 42 to again compare a newly determined concentration of glucose to the predetermined limit.

In this embodiment, the determined concentration of glucose presented at step 40 is periodically compared to predetermined limit in step 42. The periodicity may be preset in the programming or may be programmable to any desired period.

In addition, the comparison of the determined concentration of glucose may be accomplished on command as for example by activating the comparison of step 42 in response to a user command for example, based upon time or when about to consume food. Such a user command may take the form of activating a reed switch with a magnet, activating an electronic switch with a radio signal, mechanically actuating a switch by palpating the switch through the skin or many other forms that will occur to those skilled in the art; the key function of whatever action being to cause the step 42 to immediately compare the determined concentration of glucose presented at step 40 to a predetermined limit.

At step 44, the appropriate response to the high concentration of glucose is determined. The most likely appropriate response will be to activate the pump 20 to infuse an amount of insulin or other appropriate drug into the patient's blood stream. The amount of insulin to infuse may be determined by a formula or from a value retrieved in a look-up table prepared by the patient's physician. If the determined amount of insulin is determined by formula, the formula would include the variables of the determined concentration of glucose and the patient's weight as will be clear to those skilled in the art.

If the determined amount of insulin is determined from a look-up table, an appropriate responsive dose of insulin corresponding to a measured concentration of glucose and possible other variables such as the patient's weight, would be stored in the look-up table. Once the measured concentration of glucose were determined, the responsive dose of insulin would be retrieved from the look-up table.

It is intended in this embodiment that control system 14 perform steps 42, 44 and 46.

Once the responsive dose of insulin has been determined from either a formula or a look-up table, the program passed to step 48. Step 48 communicates the responsive dose to the pump 20 and the program passed to step 50. The responsive dose values communicated to the pump 20 may be transmitted to the pump 20 and stored in internal. RAM memory along with the related times of the determined doses for later uplink telemetry to a follow-up physician. Step 50 receives the responsive dose communicated from step 48 and passes it to the pump 20. The responsive dose is preferably communicated to the pump 20 by passing the appropriate responsive dose to the pump 20 through sensor telemetry module 22 (at step 48) and pump telemetry module 24 (at step 50).

Sensor telemetry module 22 is attached to flexible substrate 26. Sensor telemetry module 22 receives information about the appropriate amount of insulin to infuse into the user by pump 20 at step 44 and conveys it to pump telemetry module 24 where it is received at passed to the pump 20 at step 50. Pump 20 then infuses the appropriate amount of insulin to the patient at step 52. In the preferred embodiment, sensor telemetry module 22 and pump telemetry module 24 communicate using the body of the user itself to convey the information utilizing the electrode 32 of FIG. 4. This type of communication is sometimes referred to a "body-bus" communication.

An example of such a "body-bus" communication system is given in U.S. Pat. Nos. 4,987,897 and 5,113,859, issued to Hermann D. Funke on Jan. 29, 1991 and May 19, 1992, entitled "Body Bus Medical Device Communication System" and "Acoustic Body Bus Medical Device Communication System" respectively, the teachings of which are incorporated herein by reference in its entirety. Alternately, a radio frequency telemetry approach as described in U.S. Pat. No. 5,683,432 to Goedeke may be used. In this alternate embodiment, antenna 40 would be used to communicate to pump 20.

At step 50, the appropriate dose information is received and passed to pump 20. The program passes to step 52 where the pump administers the appropriate dose to the user. From step 52, the program passes back to step 42 to compare the newly determined concentration of glucose presented at step 40 to the predetermined limit.

Figure 3:
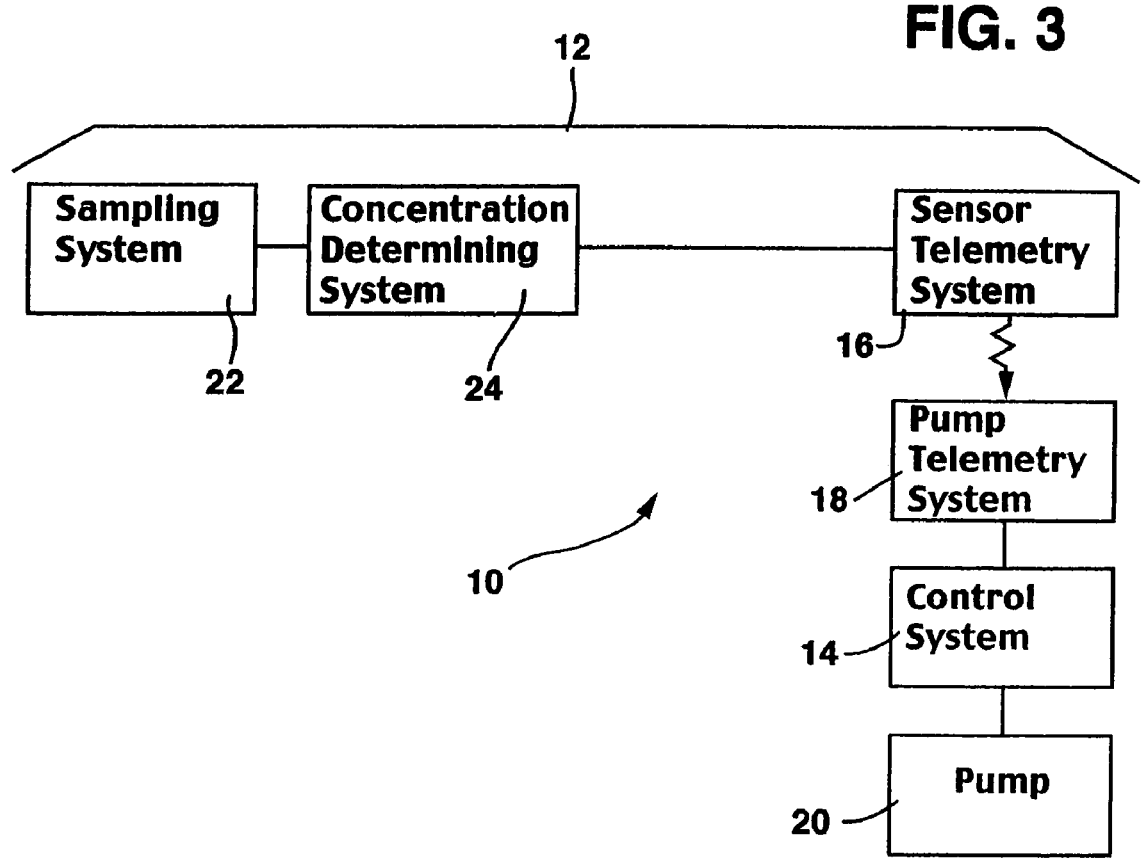
FIG. 3 is a block diagram of another embodiment of the present invention.
Figure 7:
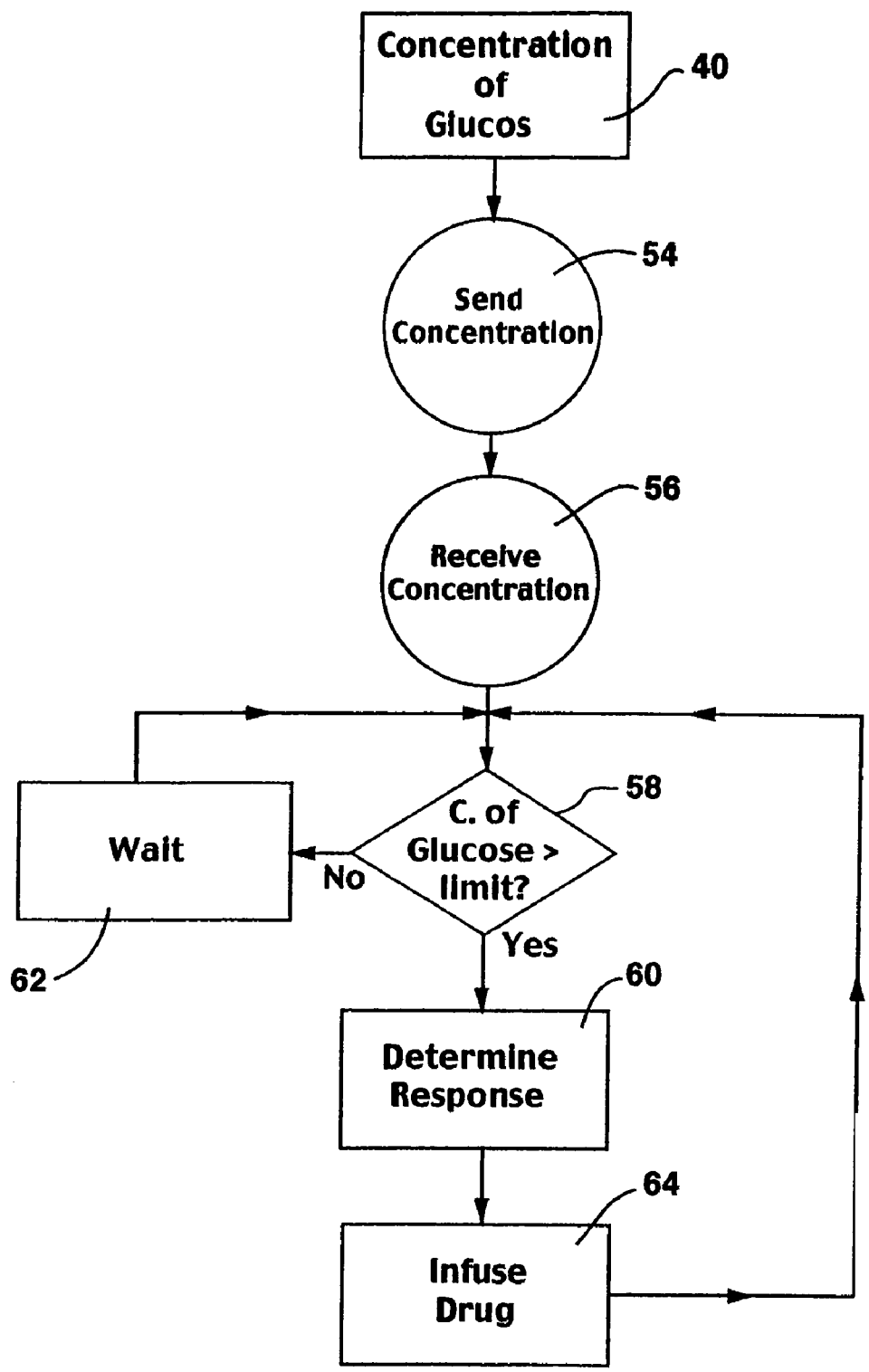
FIG. 7 is a flow chart of an alternate operation of the control system of the present invention that corresponds the embodiment shown in FIG. 3.

An alternate embodiment of the invention is shown in FIG. 3, the operation of which is shown in FIG. 7. In this embodiment, control system 14 is located with pump 20 instead of on flexible substrate 26. It is intended that control system 14 in this embodiment be part of the microprocessor or other control system that controls the operation of pump 20. However, it is also an alternate embodiment of this embodiment that the control system 14 may be a separate unit distinct from the microprocessor or other control system that controls the operation of pump 20. The key here being that the control system 14 is located with the pump 20 instead of with the flexible substrate 26.

In operation, this alternate embodiment operates as described above beginning with step 40 where the concentration of glucose determined by the sensor module 14 is presented. The program passes to step 54 where the concentration of glucose is communicated to the pump 20 via sensor telemetry module 22. The glucose concentration values communicated to the pump 20 may be transmitted to the pump 20 and stored in internal RAM memory along with the time of the determined concentration for later uplink telemetry to a follow-up physician. The program passes to step 56. Step 56 receives the concentration of glucose communicated from step 54 by pump telemetry module 24 and passes it to control system 14. Here, as above, communication between the sensor module 14 and pump 20 is accomplished by the sensor telemetry module 22 and the pump telemetry module 24 as described above. The difference in this embodiment being only that the information conveyed between the sensor module 14 and the pump 20 here is the concentration of glucose determined by the sensor module 14 instead of the appropriate dosage of insulin to be administered to the patient.

From step 56, the program passes to step 58. Step 58, in similar fashion to step 42, periodically compares the concentration of glucose presented at step 56 to a predetermined limit. If the determined concentration in step 56 exceeds the predetermined limit, the program passed to step 60. If the determined concentration in step 56 does not exceed the preset limit, no action is taken and step 58 proceeds to step 62 to wait for the appropriate period to expire before passing to step 58 to again compare a newly determined concentration of glucose received from sensor module 14 to the predetermined limit.

In this embodiment as in the preferred embodiment described above, the determined concentration of glucose is periodically compared to predetermined limit. The periodicity may be preset in the programming or may be programmable to any desired period. In addition, the comparison of the determined concentration of glucose may be accomplished on command as for example by activating the comparison of step 42 in response to a user command. As above, such a user command may take the form of activating a reed switch with a magnet, activating an electronic switch with a radio signal, mechanically actuating a switch by palpating the switch through the skin or many other forms that will occur to those skilled in the art; the key function of whatever action being to cause the step 58 to immediately compare the determined concentration of glucose to a predetermined limit.

At step 60, the appropriate response to the high concentration of glucose is determined. The most likely appropriate response will be to activate the pump 20 to infuse an amount of insulin or other appropriate drug into the patient's blood stream. Again, the amount of insulin to infuse may be determined by a formula or from a value retrieved in a look-up table. If the determined amount of insulin is determined by formula, the formula would include the variables of the determined concentration of glucose and the user's weight as will be clear to those skilled in the art.

If the determined amount of insulin is determined from a look-up table, an appropriate responsive dose of insulin corresponding to a measured concentration of glucose would be stored in the look-up table. The appropriate responsive dose would be determined based on the person's weight or other factors which will occur to those skilled in the art. Once the measured concentration of glucose is determined, the responsive dose of insulin is retrieved from the look-up table.

Once the responsive dose of insulin has been determined from either a formula or a look-up table, the program passed to step 64. At step 64, the appropriate dose information is administered to the user by pump 20. From step 64, the program passes back to step 58.

Figure 8:
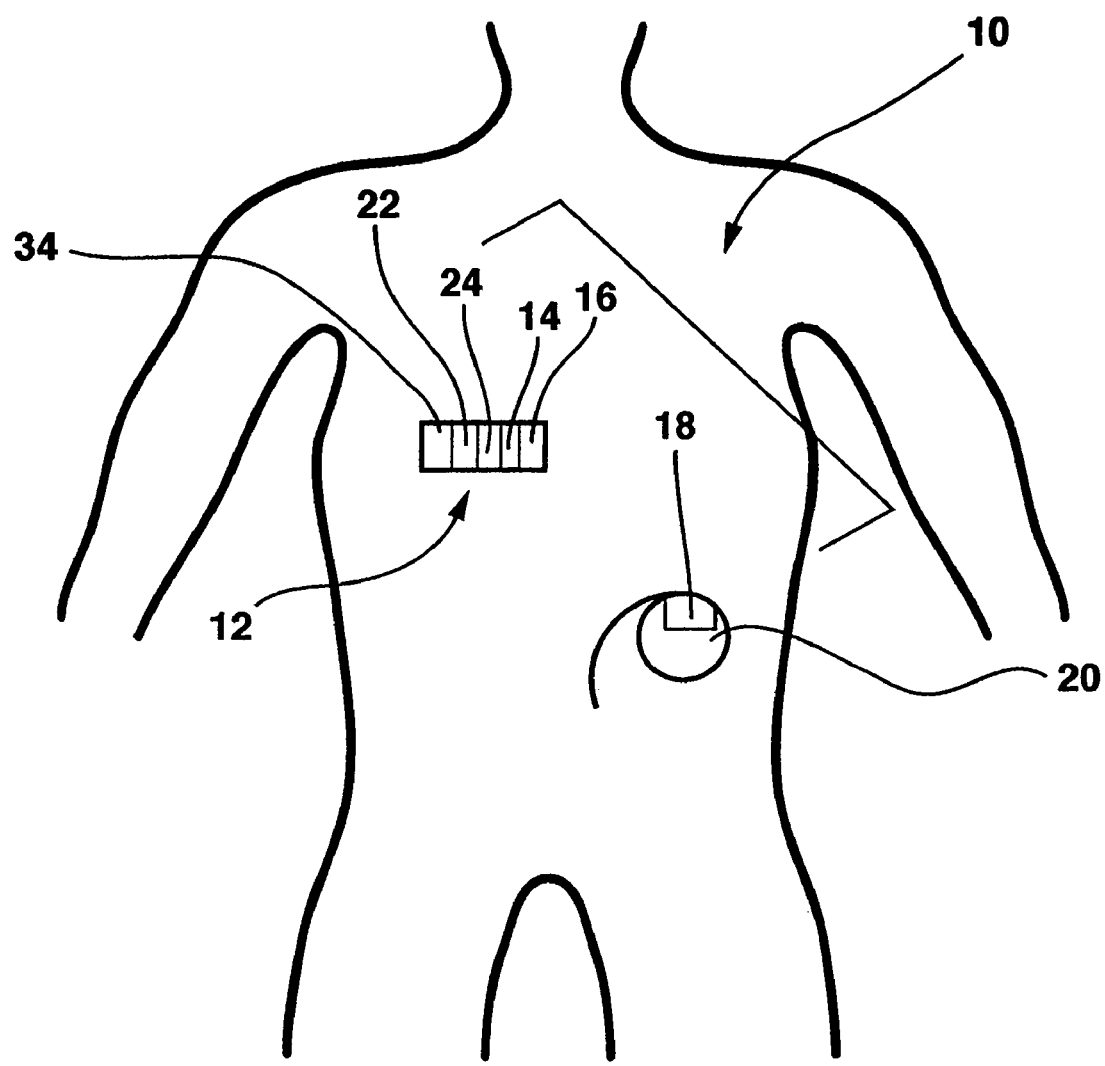
FIG. 8 is a perspective schematic view of an alternate embodiment of the present invention in use in a patient's body.

In the preferred embodiment, sensor 12 is an external sensor applied to the skin of the user. In an alternate embodiment shown in FIG. 8, sensor module 12 is implanted in the user as shown in the '186 patent issued to Peter C. Lord and Fredric C. Coleman discussed above.

In this embodiment, battery 34 may be used or may be replaced with a rechargeable battery or a "super-capacitor" to provide power to sensor module 12. Examples of appropriate rechargeable batteries include, but are not limited to lithium batteries, nickel-metal hydride, lithium polymer, nickel cadmium and rechargeable alkaline manganese dioxide. With respect to rechargeable batteries, the teaching of U.S. Pat. No. 5,661,393 issued on Aug. 26, 1997 to Upal Sengupta entitled "Circuit and Method for Detecting and Indicating the State of Charge of a Cell or Battery" is incorporated herein by reference in its entirety. Examples of "super-capacitor" power providing systems are shown in U.S. Pat. Nos. 5,591,217 issued to Francisco J. Barreras on Jan. 7, 1997 entitled "Implantable Stimulator with Replenishable High Value Capacitive Power Source and Method Therefor" and 5,733,313 issued to Francisco Jose Barreras, Sr. and Oscar Jimenez on Mar. 31, 1998 entitled "RF Coupled Implantable Medical Device with Rechargeable Back-up Power Source". The collective teachings of these patents are incorporated herein by reference.

The invention has been described primarily in connection with a device to detect glucose and deliver an appropriate response of insulin to the patient's body. It is also within the scope of the invention to detect other biological chemicals, enzymes, hormones, etc. and deliver an appropriate response of an appropriate therapeutic agent if needed. For example, the sampling system 22 and a concentration determining system 24 of the invention can also be used to sample and determine the concentration of the substances disclosed in Table 4 of the '714 Guy et al. patent, the teaching of which, including the discussion in column 12, lines 23-64, is incorporated herein by reference. In this embodiment, a particular substance of interest is sampled and its concentration determined, thereby indicating the presence and severity of a particular condition or disease as for example is shown in Table 4 of the '714 Guy et al. patent. Thereafter, the present invention delivers, as described above, an appropriate amount of an appropriate medicament or drug to the patient according to sound medical judgment.

The description contained herein is intended to be illustrative and not exhaustive. Many variations and alternatives will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A closed loop medicament pump system for a patient for sampling and determining the concentration of a substance of interest through the patient's skin and for determining and delivering a responsive dose of an appropriate medicament to the patient comprising:
an iontopheretic sensor module for sampling and detecting a concentration of a substance of interest through skin, wherein the sensor module comprises a sampling system and a concentration determining system;
a control system, responsive to the iontopheretic sensor module, for determining a response to the sampled and determined concentration of a substance of interest;
a sensor telemetry system for transmitting information regarding the response determined by the control system through the patient's body;
a pump telemetry system for receiving information regarding the response determined by the control system through the patient's body and for communicating the information to an implantable drug pump; and
an implantable drug pump, acting in response to the information communicated to the implantable drug pump from the pump telemetry system, to deliver a responsive dose of an appropriate medicament to the patient.

2. A closed loop medicament pump system according to claim 1 wherein the sensor module is an external sensor.

3. A closed loop medicament pump system according to claim 1 wherein the sensor module is disposable.

4. A closed loop medicament pump system according to claim 1 wherein the sensor module is reusable.

5. A closed loop medicament pump system according to claim 1 wherein the sensor module is attached to a flexible substrate.

6. A closed loop medicament pump system according to claim 5 wherein the flexible substrate includes an adhesive to adhere the sensor module to skin of a patient.

7. A closed loop medicament pump system according to claim 1 wherein the control system is a microprocessor.

8. A closed loop medicament pump system as in claim 7, in which the microprocessor further includes a memory with a look-up table for the responsive dose of the appropriate medicament, and the step of determining the responsive dose includes retrieving a value from the look-up table.

9. A closed loop medicament pump system as in claim 7, in which the microprocessor further includes a memory with a formula for the responsive dose of the appropriate medicament, and the step of determining the responsive dose includes determining the dose according to the formula.

10. A closed loop medicament pump system as in claim 9, in which the formula includes the variables of the determined concentration of the substance of interest and the patient's weight.

11. A closed loop medicament pump system as in claim 7, in which the drug pump includes memory, and the information communicated to the pump to cause the drug pump to deliver the responsive dose of the appropriate medicament is stored in the memory.

12. A closed loop medicament pump system as in claim 11, in which the information is stored in the memory with related time of the delivery of the responsive dose.

13. A closed loop medicament pump system as in claim 11, in which the information is stored in the memory with related time of the delivery of the responsive dose and the memory keeps the information and time available for later uplink telemetry.

14. A closed loop medicament pump system as in claim 13, further comprising uplink telemetry equipment.

15. A closed loop medicament pump system as in claim 7, wherein the microprocessor operates a program including the steps of receiving information related to the concentration of the substance of interest, comparing the information related to the concentration to information related to a predetermined limit, and then, if the comparing step indicates the concentration exceeds the predetermined limit, determining the appropriate response to the determined concentration.

16. A closed loop madicament pump system as in claim 15, in which the operation of the program steps of receiving information related to the concentration of the substance of interest and comparing the information related to the concentration to information related to the predetermined limit may be accomplished on command.

17. A closed loop medicament pump system as in claim 15, in which the system, pump or medical device includes a patient command means and the operation of the program steps of receiving information related to the concentration to substance of interest and comparing the information related to the concentration to information related to the predetermined limit may be accomplished on patient command through the patient command means.

18. A closed loop medicament pump system as in claim 15, wherein the program further includes the step of generating information to cause the drug pump to deliver the responsive dose of the appropriate medicament.

19. A closed loop medicament pump system as in claim 15, wherein the program further includes the step, if the comparing step indicates the concentration does not exceed the predetermined limit, waiting for a period of time to expire before again operating the program steps of receiving information related to the concentration of the substance of interest and comparing the information related to the concentration to information related to the predetermined limit.

20. A closed loop medicament pump system as in claim 19, in which the periodicity of the operation of the program, including the period of time for waiting, may be present in the program.

21. A closed loop medicament pump system as in claim 19, in which the periodicity of the operation of the program, including the period of time for waiting, is programmable.

22. A closed loop medicament pump system as in claim 1, the drug pump acting in response to communication to the drug pump by body bus.

23. A closed loop medicament pump system as in claim 1, the drug pump acting in response to communication to the drug pump by radio telemetry.

24. A closed loop medicament pump system as in claim 1, further comprising an operatively connected antenna which receives downlinked telemetry programming data transmitted by an external programmer.

25. A closed loop medicament pump system as in claim 1, further comprising an operatively connected battery.

26. A closed loop medicament pump system, pump or medical device as in claim 25 wherein the battery is a flexible battery.

27. A closed loop medicament pump system as in claim 1, in which the control system is located with the drug pump.

28. A closed loop medicament pump system as in claim 1, in which the control system is located with the sensor module.

29. A closed loop medicament pump system according to claim 1 wherein the substance of interest includes glucose and the sensor module samples and detects a concentration of the substance of interest including glucose.

30. A closed loop medicament pump system according to claim 1 wherein the appropriate medicament is insulin, and the drug pump delivers insulin.

* * * * *

UNITED STATES PATENT AND TRADEMARK OFFICE
CERTIFICATE OF CORRECTION

| | | |
|---|---|---|
| PATENT NO. | : 7,429,255 B2 | Page 1 of 1 |
| APPLICATION NO. | : 10/747832 | |
| DATED | : September 30, 2008 | |
| INVENTOR(S) | : David L. Thompson | |

It is certified that error appears in the above-identified patent and that said Letters Patent is hereby corrected as shown below:

Col. 10, Line 17, Claim 17: "concentration to substance" should be deleted - should read --concentration of the substance--.

Signed and Sealed this

Tenth Day of November, 2009

David J. Kappos
*Director of the United States Patent and Trademark Office*